United States Patent
Krishnan et al.

(10) Patent No.: US 10,849,983 B2
(45) Date of Patent: Dec. 1, 2020

(54) DEVELOPMENT OF SOLUBLE ALBUMINATED CURCUMIN FOR APPLICATION IN CANCER THERAPY

(71) Applicants: Sree Chitra Tirunal Institute for Medical Sciences and Technology, Thiruvananthapuram (IN); Indian Council of Medical Research, New Delhi (IN)

(72) Inventors: Lissy Kalliyana Krishnan, Thiruvananthapuram (IN); Christina Thomas, Thiruvananthapuram (IN)

(73) Assignees: Sree Chitra Tirunal Institute for Medical Sciences and Technology, Thiruvananthapuram (IN); Indian Council of Medical Research, New Delhi (IN)

( * ) Notice: Subject to any disclaimer, the term of this patent is extended or adjusted under 35 U.S.C. 154(b) by 104 days.

(21) Appl. No.: 14/892,164

(22) PCT Filed: May 20, 2014

(86) PCT No.: PCT/IN2014/000338
§ 371 (c)(1),
(2) Date: Nov. 18, 2015

(87) PCT Pub. No.: WO2014/192024
PCT Pub. Date: Dec. 4, 2014

(65) Prior Publication Data
US 2016/0129127 A1 May 12, 2016

(30) Foreign Application Priority Data
May 20, 2013 (IN) .......................... 2200/CHE/2013

(51) Int. Cl.
*A61K 47/64* (2017.01)
*A61K 31/12* (2006.01)

(52) U.S. Cl.
CPC ............ *A61K 47/643* (2017.08); *A61K 31/12* (2013.01)

(58) Field of Classification Search
None
See application file for complete search history.

(56) References Cited

U.S. PATENT DOCUMENTS 4,368,208 A 1/1983 Schranz
2007/0270464 A1 11/2007 Liotta et al.

FOREIGN PATENT DOCUMENTS

| CN | 103054810 A | 4/2013 |
|---|---|---|
| WO | 2004080396 A2 | 9/2004 |
| WO | 2007098504 A1 | 8/2007 |
| WO | 2010057503 A2 | 5/2010 |

OTHER PUBLICATIONS

Ambion 2013 Life Technologies Ultrapure BSA: 2 pages. (Year: 2013).*
Lin, S-S., et al. 2008 Cancer Letters 272: 77-90. (Year: 2008).*
Hilchie, A.L., et al. 2010 Nutrition and Cancer 62(3): 379-389. (Year: 2010).*
Gururaj, A.E., et al. 2002 Biochemical and Biophysical Research Communications 297: 934-942. (Year: 2002).*
Hui, X-J., et al. 2008 Chinese Journal of Laboratory Diagnosis: Curcumin induces K562 cell apoptosis and has effects on cell cycle phases abstract (1 page). (Year: 2008).*
Berg, J.M., et al. 2002 Biochemistry Section 4.1: The purification of proteins is an essential first step in understanding their function : 11 pages. (obtained from the internet Dec. 18, 2018). (Year: 2002).*
O'Fágáin, C., et al. 2011 Protein Chromatography: Methods and Protocols, Methods in Molecular Biology vol. 681: 25-33. (Year: 2011).*
PanReac AppliChem Albumin (BSA) product sheets 2010: 2 pages. (Year: 2010).*
Barik, A., et al. 2007 Chemical Physics Letters 436: 239-243. (Year: 2007).*
Kunwar, A., et al. 2006 Biochimica et Biophysica Acta 1760: 1513-1520. (Year: 2006).*
Barik et al., "Photophysical Studies on Binding of Curcumin to Bovine Serum Albumin", Photochemistry and Photobiology, 2003, pp. 597-603, vol. 77, No. 6.
Bourassa et al., "Resveratrol, Genistein, and Curcumin Bind Bovine Serum Albumin", Journal of Physical Chemistry B, 2010, pp. 3348-3354, vol. 114, No. 9.
Kooshk et al., "In Vitro Anti-Cancer Activity of Native Curcumin and 'Protein-Curcumin' Systems: A Perspective on Drug-Delivery Application", Journal of Reports in Pharmaceutical Sciences, 2013, pp. 66-74, vol. 2, No. 1.
Kumar et al., "Biodegradable Microspheres of Curcumin for Treatment of Inflammation", Indian Journal of Physiology and Pharmacology, 2002, pp. 209-217, vol. 46, No. 2.
Maiti et al., "Curcumin-phospholipid complex: Preparation, therapeutic evaluation and pharmacokinetic study in rats", International Journal of Pharmaceutics, 2007, pp. 155-163, vol. 330.
Mitra, Sankar P., "Binding and Stability of Curcumin in Presence of Bovine Serum Albumin", Journal of Surface Science and Technology, 2007, pp. 91-110, vol. 23, No. 3-4.
Tonnesen et al., "Studies of curcumin and curcuminoids. XXVII. Cyclodextrin complexation: solubility, chemical and photochemical stability", International Journal of Pharmaceutics, 2002, pp. 127-135, vol. 244.

* cited by examiner

*Primary Examiner* — Marsha Tsay
(74) *Attorney, Agent, or Firm* — The Webb Law Firm (57) ABSTRACT

This invention relates to an albumin-curcumin conjugate for application in cancer therapy, including albumin and curcumin.

11 Claims, 6 Drawing Sheets

Fig 1. Summary of the process of conjugate preparation and evaluation of the product

Fig2. Spectral Properties of the conjugate. A. UV-Vis spectra. Tracings shown are of curcumin and Alb-Curc. The Alb-Curc was the product purified by gel filtration chromatography. Peak height of Curc and Alb-Curc are almost the same. Fig 2 B. FT-IR spectrum. Tracings are curcumin(top), albuminated curcumin (middle) and albumin (bottom)

Fig 3. Appearance of the product A, lyophilized Alb-Curc with different binding ratio; B, re dissolved Alb-Curc after lyophilization with different conjugation strength.

Fig4. Effect of conjugate on PC3 morphology. Dose Response- PC3 cultures with and without conjugate. Cultures were treated with the drug after it became confluent. Graded concentration of drug added to each well is indicated in the image. The cell density is the least and similar to positive control (2 µM Doxorubicin) when Alb-Curc added was 100 µM (F) indicating cell death. All images were taken at the same magnification. Scale bar is shown at the right hand corner of each image.

Fig 5. Live/dead cell assay. Flow cytometry of treated cells. The data shown is of PC3 cells and the concentration of the drug conjugate added is shown in the graph. The assay was done after 24h incubation of the drug with PC3 culture. FITC conjugated Annexin V and PI staining was done as per the manufacturers' instruction. Control cells stained with the reagent kit is shown and increase of apoptotic cell in Q4 and dead cell in Q1 and apoptotic dead cells in Q2 were compared to that of the stained negative control for each period and each drug concentration.

Fig 6. Effect of conjugate on lung cancer cells: Alb-curc treated A549 cultures. Cultures were treated with the drug after it became confluent. Concentration of Alb-Curc added is indicated in the image. All images were taken at the same magnification. Maximum cell death at 100uM concentration is indicated. Positive control is cells treated with standard drug doxorubicin Fig 7. Histograms of cell cycle assay. Histograms acquired in FACS Aria and analyzed by Flojo software are shown. The cell type and concentration of drug used are indicated in the respective image. Cells in the log phase were treated with drug for 24h and cycle was analyzed. Cell cycle arrest in S-phase is indicated Fig.8 Effect of conjugate on K652 culture: Morphology of cells with and without Alb-Curc conjugate. Cultures were treated with the drug after it became confluent. Concentration of Alb-Curc added is indicated in the image. All images were taken at the same magnification. At 1000uM cell death is comparable with positive control (Doxorubicin)

Fig 9 Effect of conjugate on primary endothelial cell growth: Representative Photomicrographs of EC cultures. Monolayers of EC were treated with each drug type. A, EC treated with 250 uM of free Curc added into the culture from the DMSO stock ( 2.5 ul of 0.2M stock to 2ml culture medium) - there is minimal effect with few round cells; B, positive control into which doxorubicin (2 µM) was added; C, EC treated with 100uM Alb-Curc; D, EC treated with 250uM Alb-Curc in which all ECs rounded off and died. All monolayers were treated with respective drug for 24 h.

Fig 10 Effect of Conjugate on primary fibroblasts: Representative Photomicrographs of Fibroblast cultures. Monolayers of fibroblast were treated with drug concentrations as shown in the image. Untreated monolayer is the negative control and doxorubicin (2 µM) treated culture is the positive control. All photographs were taken at the same magnification. The drug was treated with cells for 24h in each case. The cells treated with 50uM Alb-Curc maintained same morphology and density as the untreated negative control. With 100 uM conjugate, cell density is reduced but fibroblast morphology is intact.

DEVELOPMENT OF SOLUBLE ALBUMINATED CURCUMIN FOR APPLICATION IN CANCER THERAPY

CROSS-REFERENCE TO RELATED APPLICATIONS

This application is the United States national phase of International Application No. PCT/IN2014/000338 filed May 20, 2014, and claims priority to Indian Patent Application No. 2200/CHE/2013 filed May 20, 2013, the disclosures of which are hereby incorporated in their entirety by reference.

FIELD OF THE INVENTION

This invention relates to an albuminated curcumin for application in cancer therapy.

BACKGROUND OF THE INVENTION

Science is catching up in news with its stupendous rise in research on turmeric, more significantly the curcumin evolving as the super food in coming years.

Curcumin is a low molecular weight polyphenol obtained from the roots of *Curcuma longa* notable for its immense potential to treat various dreadful diseases with its wide spectrum of biological functions such as anti cancerous effect, antiinflammatory, antioxidant coupled with the hepato- and nephro-protective, antithrombotic, myocardial infarction protective analgesic and antirheumatic effects of curcumin are also well acknowledged. In addition to its aromatic, stimulant and coloring properties in the diet, turmeric is mixed with other natural compounds such as slaked lime and has been used topically as a treatment for wounds, inflammation and tumor.

Curcumin exhibits great promise as a therapeutic agent, and is currently being experimented in clinical trials for a variety of conditions including multiple myeloma, pancreatic cancer, myelodysplastic syndromes, colon cancer, psoriasis and Alzheimer's disease in humans.

Curcumin is remarkably non-toxic, but exhibits limited bioavailability. This poor solubility has been highlighted as a major limitation in clinical use.

Consequently search for a "supercurcumin" without these problems and with efficacy equal to or better than that of native curcumin is ongoing. Innovative methods of cancer treatment require new concepts of drug delivery in cancer. There is a vast range of strategies available for drug delivery in cancer. To improve the bioavailability of curcumin, numerous approaches have been undertaken. These approaches involve the use of adjuvants like pipeline that interferes with glucuronidation, liposomal curcumin, nanoparticles, curcumin phospholipid complexes and the use of structural analogues of curcumin. Recent progress in nanoparticle engineering has certainly improved drug targeting, but the results are not as good as expected. This is largely due to the fact that nanoparticles, regardless of how advanced they are, find the target through blood circulation, like the conventional drug delivery systems do. The accumulation of nanoparticles in cells, their toxicity and clearance are issues that are not addressed satisfactorily.

Exhaustive work has been carried out to improve the bioavailability of curcumin owing to its low aqueous solubility and low absorption in systemic circulation. With the advent of nanotechnology, attempts have been made to increase the curcumin bioavailability by engulfing it with nanocarriers, polymeric nanoparticles, solid lipid nanoparticles, micelles, nanogels, nano suspensions, nanoemulsions, complexes and dendrimer/dimer. This certainly has improved drug targeting. But the results are not so encouraging, owing to the big size of nanoparticles, they are found to be less efficient in passing through the blood vessels which drastically decrease the amount of nanoparticle leaking into the tumor tissue whereas native albumin is more efficient in accumulating in tumour tissue.

Extensive work has been done on the preparation of water-soluble curcumin by incorporation into various surfactant micellar systems; (e.g. sodium dodecyl sulfate, cetylpyridinium bromide, gelatine, polysaccharides, polyethylene glycol and cyclodextrins) have been reported (Maiti et al., 2007, Tonnesen et al., 2002). In another approach, water soluble curcumin complex was synthesized by dissolving and mixing curcumin and gelatin in an aqueous acetic acid solution (U.S. Pat. No. 4,368,208). All these techniques involve the release of curcumin from the delivery vehicle which poses the major problem of premature drug release, i.e. drug release can occur before reaching the target site. None of the approaches threw light on the molecular mechanisms and experimental data for recommended dosing patterns necessary for destroying the cancer cells. The current study focuses on a water soluble, nonrelease form of curcumin and its effects in the inhibition of proliferation and induction of death of human cancer cells. This also gave insight into the recommended dosing regimen as well as the stable binding of curcumin and plasma protein alleviating the problems of drug release.

Though curcumin which is an extensively studied polyphenol, not much work has been done on direct conjugation of curcumin with a native bio-friendly carrier albumin.

Objects of the Invention

It is therefore an object of this invention to provide an albuminated curcumin which has increased aqueous solubility.

It is a further object of this invention to provide an albuminated curcumin which has increased bioavailability.

Another object of this invention is to provide an albuminated curcumin, which does not degrade easily.

Yet another object of this invention is to provide an albuminated curcumin, which is pure and stable.

These and, other objects of the invention will be apparent from the ensuing description, when read in conjunction with the accompanying drawings.

DETAILED DESCRIPTION OF THE INVENTION

Thus according to this invention is provided an albuminated curcumin for prospective application in cancer therapy.

In accordance with this invention different concentrations of bovine serum albumin (BSA) were conjugated with incremental concentrations of curcumin and the best parameter for obtaining high curcumin solubility was identified.

Albumin solution and dissolved curcumin are taken and mixed at high concentration but low volume of DMSO. The mixture is gel filtered through sephadex G-25 to remove un-reacted curcumin.

The binding ratio was calculated with the help of diode array spectrophotometer 8453. The spectral peak ratio of albumin (280 nm) and curcumin (420 nm) was used to estimate binding efficiency; the lower ratio, the higher is the binding.

The primary objective was to standardize conditions for preparation of albumin-curcumin (alb-cur) complex and to establish purity of the conjugate, yield, stability and activity. Parameters tested were the effect of component concentration, pH of the reaction mixture, time of reaction and temperature of reaction, on the binding efficiency. Other aims were to establish conjugation of curcumin to albumin by spectroscopic methods, prove stability and solubility of the bound curcumin and demonstrate biological activity of the complex on cancer cell lines and primary human cells in vitro.

Conjugation of Curcumin to Albumin

Different concentrations of bovine serum albumin (BSA) were mixed with varying concentrations of curcumin and the conjugate was purified from un-reacted molecules using gel filtration chromatography. The conjugate was analyzed for specific spectral peaks for albumin (280 nm) and curcumin (420 nm). Ratio of A280/A420 indicated the binding efficiency.

Preparation of Conjugate

Figure 1:
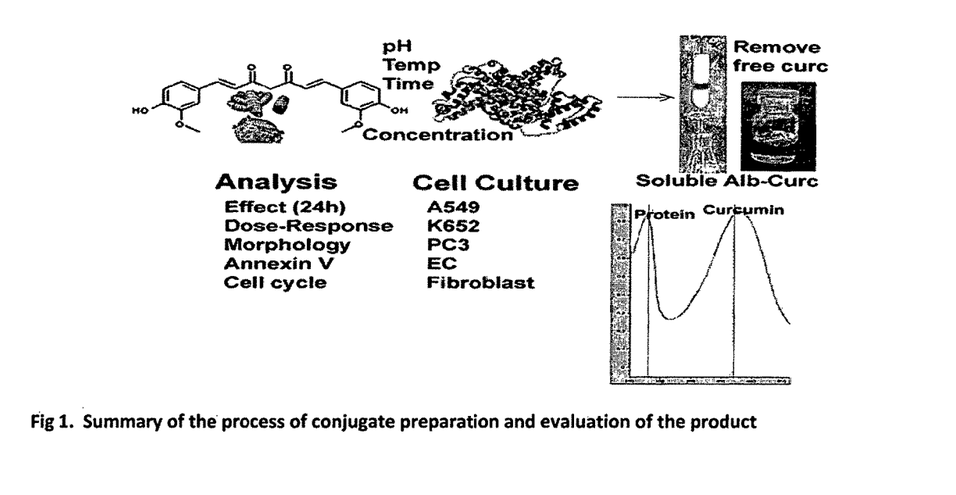
FIG. 1. Summary of the process of conjugate preparation.

BSA (20-50 mg) was dissolved in 5 ml to 10 ml of phosphate buffered saline (PBS) at pH 6-10 with gentle stirring. Curcumin, 0.01 volume of high concentration (about 1-2M) stock, in DMSO were added to BSA. The column was packed with Sephadex G-25 beads and equilibrated with the buffer. After predefined periods of incubation at specified temperature albumin-curcumin mixture was loaded onto the column, and was eluted in PBS. The peak that eluted the conjugate was identified by measuring A280 and 420 nm of 1 ml fractions. The fractions which showed minimum A280/A420 ratio were pooled and used for further evaluations. See FIG. 1.

Conjugate Characterization

Figure 2:
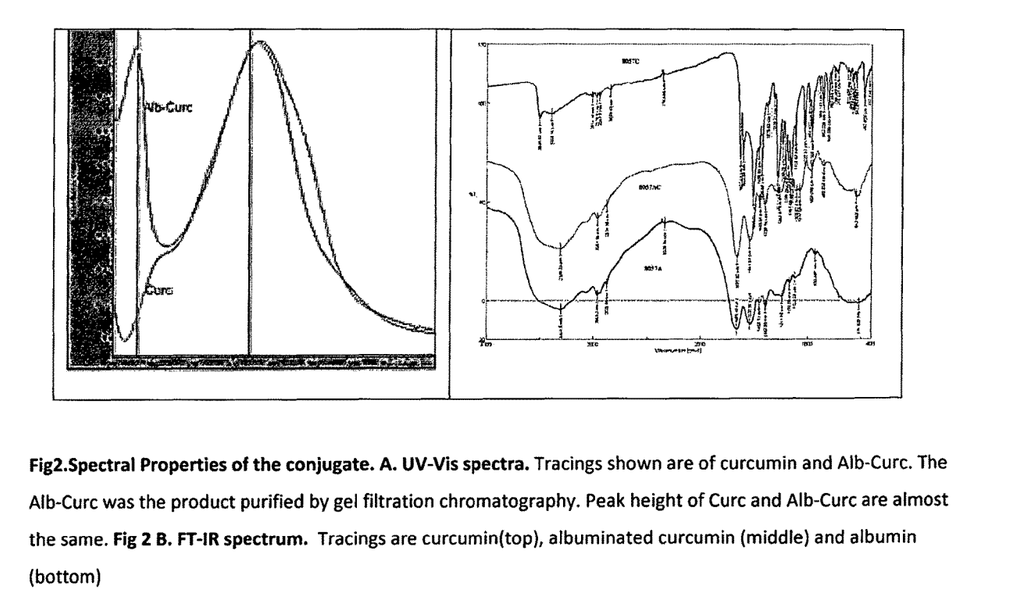
FIG. 2. Spectral properties of the conjugate.

Characterization of conjugated product was carried out with UV-visible absorption soectroscopy (diode array spectrophotometer, Hewlett Packard 8453), infrared (Jasco 6300 FT-IR spectrometer)/Raman spectroscopy (Bruker RFS 100/s FT-Raman spectroscope). See FIG. 2.

Detection of curcumin concentration bound to Albumin Purified, pooled conjugate was dispensed into 1 ml fractions and lyophilized. To extract the bound curcumin, DMSO was added to extract curcumin from the conjugate, vortex mixed, centrifuged to remove the protein debris and the absorbance of the supernatant was estimated at 420 nm (Max absorption of curcumin) in a diode array spectrophotometer. For quantification of the extracted curcumin, a standard curve was prepared using different concentrations of curcumin in DMSO.

Release Of Curcumin From Albumin

To prove the stability of the conjugate, the free curcumin that might have generated from the conjugate was analyzed. The gel filtered conjugate was filled in dialysis bags and were suspended in 1 ml PBS, pH 7.4 in cryovials and placed in a vibratory shaker at 4° C. At regular intervals such as 5 min, 24h, 48h and 72h, the dialysate was analyzed for detection of curcumin-specific spectral peak.

Maintenance Of Cell Lines

To study the effect of the drug conjugate on cancer cells, Lung (A549), Leukemia (K562), & Prostate (PC-3) cell lines were procured from NCCS, Pune. On receipt, the cell lines were sub cultured and sufficient numbers of vials were stored in −800° C. deep freezer. To study the effect of curcumin on angiogenesis, primary endothelial cells isolated from sheep was used. The effects on primary human fibroblast cells were also studied. Each cell line was maintained in their respective recommended media. A549, PC3 and fibroblast cells were maintained in DMEM media with 10% FBS. K562 cells were maintained in IMDM media supplemented with 10% FBS and endothelial cells in MCDB media with 10% FBS, L-ascorbic acid, VEGF and L-Glutamine.

Estimation of Apoptosis and Cell Cycle Arrest by Flow Cytometry

The effect of curcumin was analyzed on cell apoptosis and cycle arrest. Different concentrations of the alb-cur conjugate were added into the cultures. The concentrations employed were 250 µM, 500 µM, and 1000 µM which were achieved by adding stock prepared by dissolving lyophilized curcumin-albumin conjugate.

Results

Effects of Temperature, pH and reaction time on curcumin binding to albumin

Binding mixture was kept at 4° C., 37° C. and 28° C.

$$\text{Binding Ratio} = \frac{\text{Absorbance at 280 nm}}{\text{Absorbance at 420 nm}}$$

The best binding was obtained at 37° C.

Reaction was allowed at different pH such as 7,8,9 and 10. The best pH for binding was found to be at pH 7.2. Incubation of reaction mixture at pH 7.2 at 37° C.±2° C. and incubated for 1 and 2 hours indicated that there was no significant change in the binding ratio with time.

Effect of Concentration of Curcumin on Binding

Different concentrations of curcumin (25 µM, 50 µM, 200 µM, 300 µM, and 500 µM, 1000 µM, 2000 µM) were added to albumin (constant concentration 50 mg protein/ml at pH 7.2, 37° C. and incubation time of 1 hour. With the increasing concentration of curcumin the binding rate increased and the best spectral ratio of curcumin was obtained when 2000 µM was added to 1 ml of solution containing 50 mg of albumin.

Effect of Concentration of Protein on Binding

Figure 3:
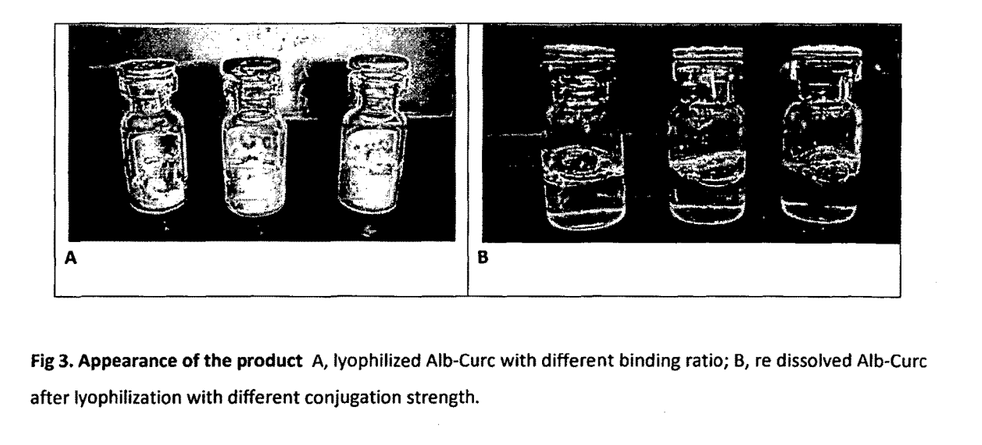
FIG. 3. Appearance of the product.

Various concentrations of protein (10 mg, 20 mg, 50 mg and 100 mg), after keeping the curcumin concentration constant, at pH 7.2 & 37° C. for 1 hour incubation was also evaluated for binding efficiency. Binding was found to increase with increase of protein concentration. The best concentration was identified to be 50 mg. Dissolution of 100 mg in 1 ml was impossible so for all further studies 50 mg albumin & 2000 µM curcumin were mixed to prepare the conjugate. High solubility of the alb-cur conjugate is visible from the clear solutions of the Alb-cur conjugate dissolved in PBS (FIG. 3).

The invention will now be explained in greater detail with the help of the non-limiting examples.

EXAMPLE 1

BSA 20 mg was dissolved in 1 ml of phosphate buffered saline (PBS) at pH 7.2 with gentle stirring. Curcumin 200 µM, in 10 µl DMSO was added to BSA. A column was packed with Sephadex G-25 beads and equilibrated with the buffer. After 1 hour of incubation at 37° C., albumin-curcumin mixture was loaded onto the column, and was eluted in PBS. The peak that eluted the conjugate was identified by measuring A280 and 420 nm of 1 ml fractions. The fractions which showed minimum A280/A420 ratio were pooled.

EXAMPLE 2

BSA 50 mg was dissolved in 1 ml of phosphate buffered saline (PBS) at pH 7.2 with gentle stirring. Curcumin 2000 µM, in 10 µl DMSO was added to BSA. A column was packed with Sephadex G-25 beads and equilibrated with the buffer. After 1 hour of incubation at 37° C., albumin-curcumin mixture was loaded onto the column, and was eluted in PBS. The peak that eluted the conjugate was identified by measuring A280 and 420 nm of 1 ml fractions. The fractions which showed minimum A280/A420 ratio were pooled.

Characterization of Conjugate by UV, FT-IR and Raman Soectroscopy)

FT-IR and Raman spectroscopy were done and the overlaid spectra were obtained which confirmed the presence of albumin and curcumin in the conjugate (FIG. 2B). Detectable absorption peak of curcumin was observed at 420 nm which confirms the incorporation of curcumin to albumin. With increasing conc. of curcumin used for conjugation with albumin, there was increase in the quantity of incorporated curcumin, which is evident from spectral height at 420 nm (FIG. 2A).

Curcumin extracted from the lyophilized conjugate to DMSO indicated that nearly 70 to 80% of the added curcumin in the reaction mixture was complexed with albumin, when the concentration of the latter was 50 mg/ml:

| Curcumin quantity added (µM) | Curcumin extracted into DMSO (µM) |
| --- | --- |
| 50 | 38 |
| 250 | 184 |
| 500 | 368 |
| 1000 | 735 |

However high or low was the concentration of curcumin added to albumin, a portion of the drug remained unbound, which was removed by gel filtration chromatography.

Cell Culture Studies

Figure 4:
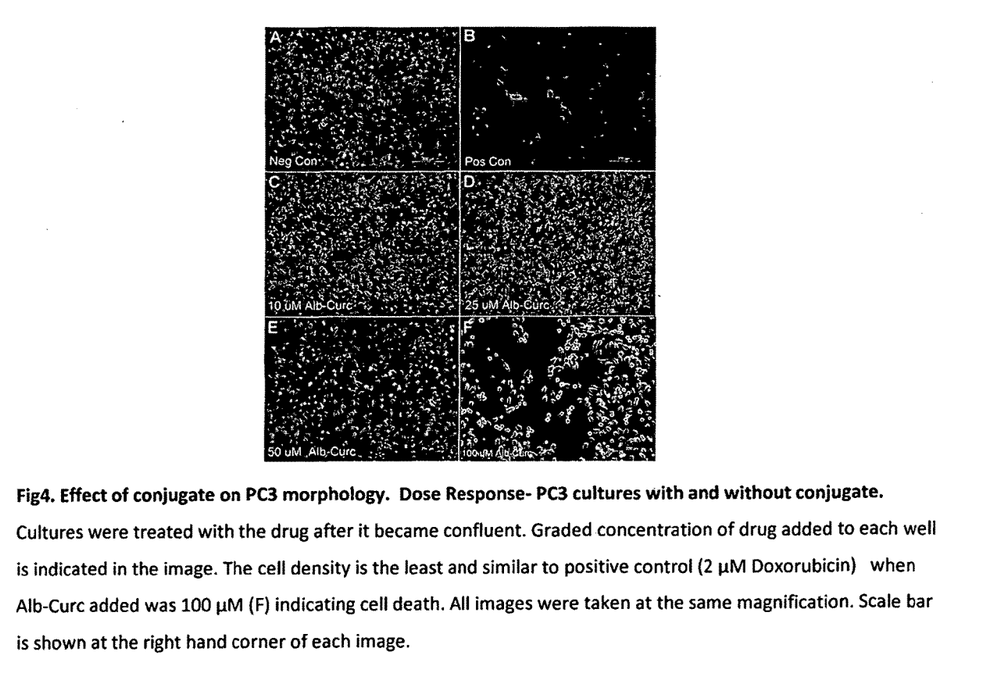
FIG. 4. Effect of conjugate on PC3 morphology.
Figure 5:
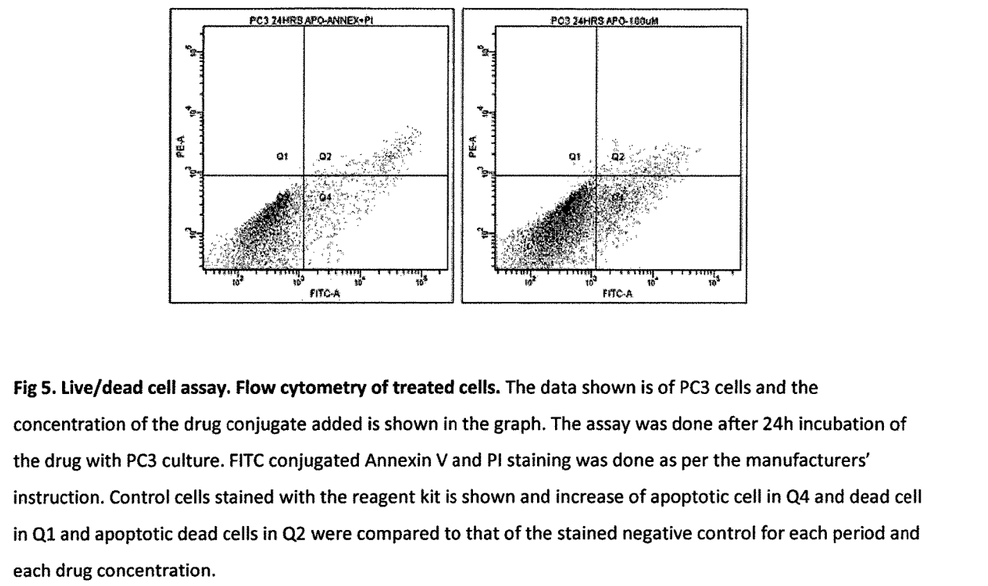
FIG. 5. Live/dead cell assay.
Figure 6:
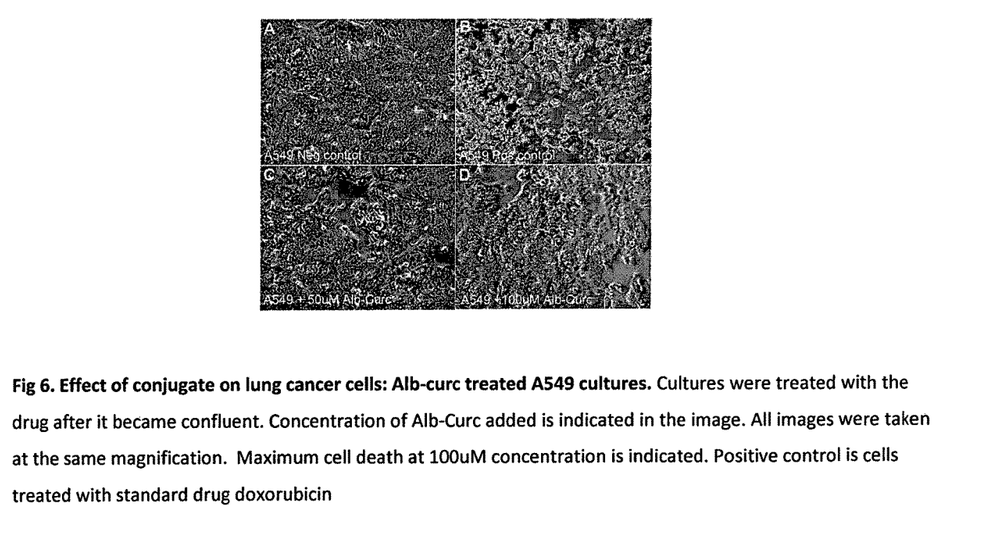
FIG. 6. Effect of conjugate on lung cancer cells.
Figure 7:
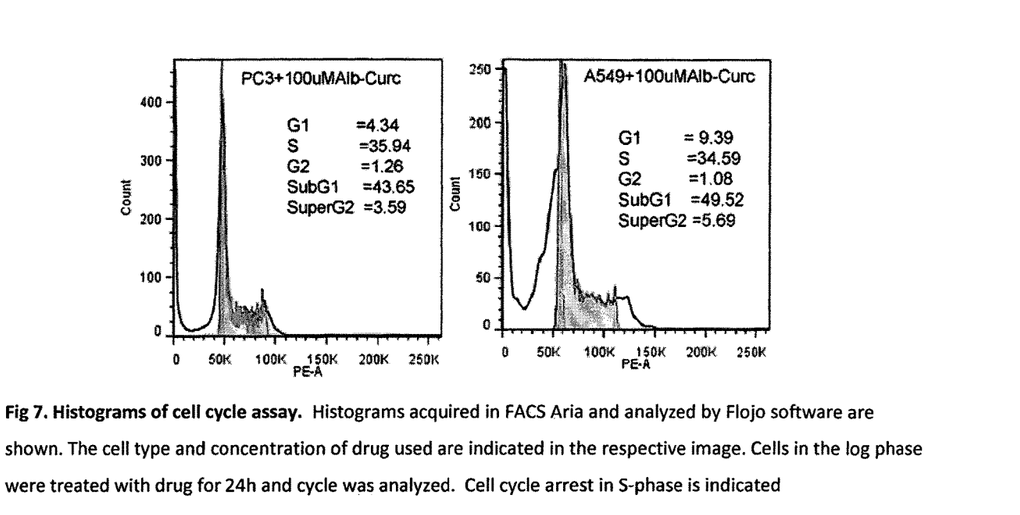
FIG. 7. Histograms of cell cycle assay.
Figure 8:
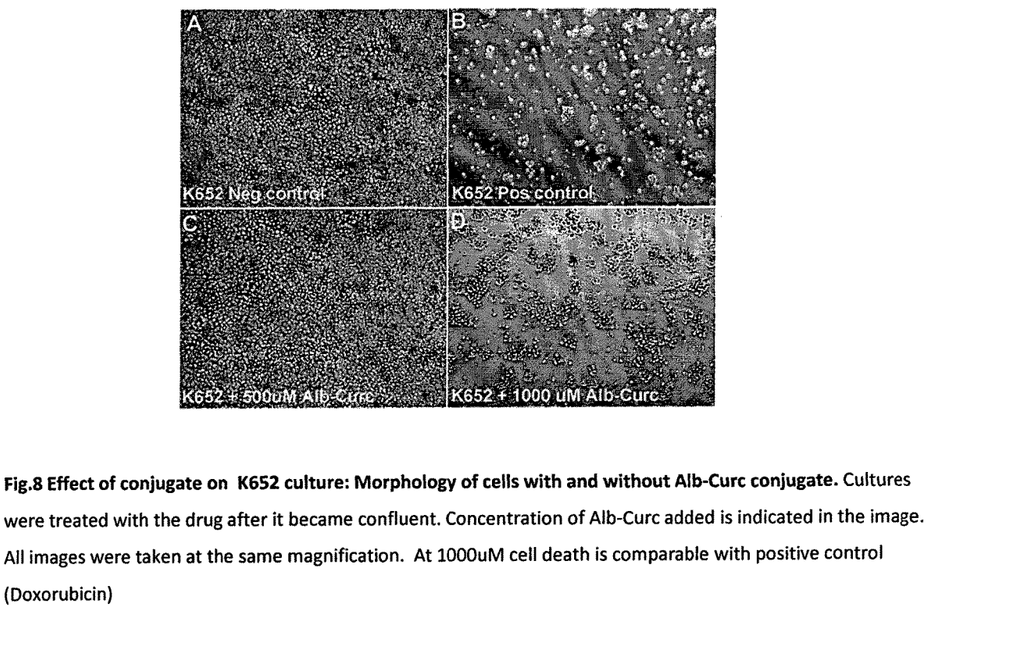
FIG. 8. Effect of conjugate on K562 culture.

The efficacy of the loaded drug was analyzed using solid tumor cell lines of prostate cancer (PC-3) [FIGS. 4 & 5] lung cancer (A549) [FIGS. 6 & 7B] and suspension cell line of leukemia (K562) [FIGS. 7A & 8]. The toxicity of the conjugated albumin-curcumin complex was assed by Live/Dead assay using Annexin V in primary fibroblasts. A graded concentration of alb-cur complex was used for the study and the optimum dose was standardized for the normal cell survival and growth.

The stock concentration of conjugate used was 2000 µM [Curcumin]

a) PC-3 Cells (Phase Contrast Microscopy)-24h

The Alb-cur conjugate showed promising results to prostate cancer cells.

(FIGS. 4 & 5). A dose and time dependent apoptosis was seen. 500 and 1000 µM concentration, showed apoptotic effects, but the cur/DMSO showed normal morphological features which highlights the non-solubility of curcumin and the difficulty of uptake by the cells.

b) A549 (Lung Cancer Cells)-24h Phase Contrast Microscopy) and Cell Cycle Analysis on A549 Cells-48h The histogram of the cell cycle suggests (FIGS. 6 & 7B) that there is a slight increase in the population of cells in the S phase in 5-FU treated (Positive ctrl) cells and increase of cells in the Sub $G_0$ phase in 250 and 500 µM Alb-cur complex treated cells. The data was analyzed using Flowjo software.

c) K562 (Human Leukemia Cells)-72h Phase Contrast Microscopy

The results showed resistance of the leukemic cells towards the drug at lower concentrations but with 1000 µM albumin-curcumin conjugate, cell density was lower which indicate reduced cell proliferation (FIG. 8).

d) Endothelial Cells-24h

Figure 9:
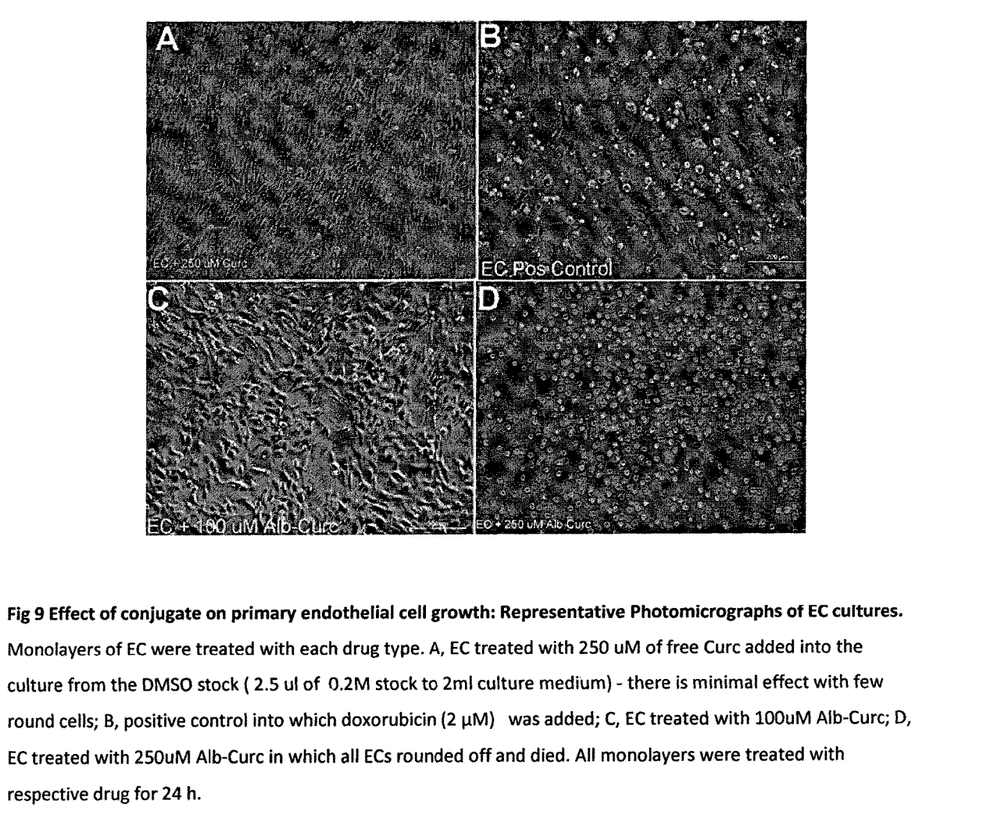
FIG. 9. Effect of conjugate on endothelial cell growth.

The figures (FIG. 9) suggests the antiangiogenic effects induced by the drug on endothelial cells which is very promising in treating metastasis in cancer therapy.

e) Fibroblast Cells-48h

Figure 10:
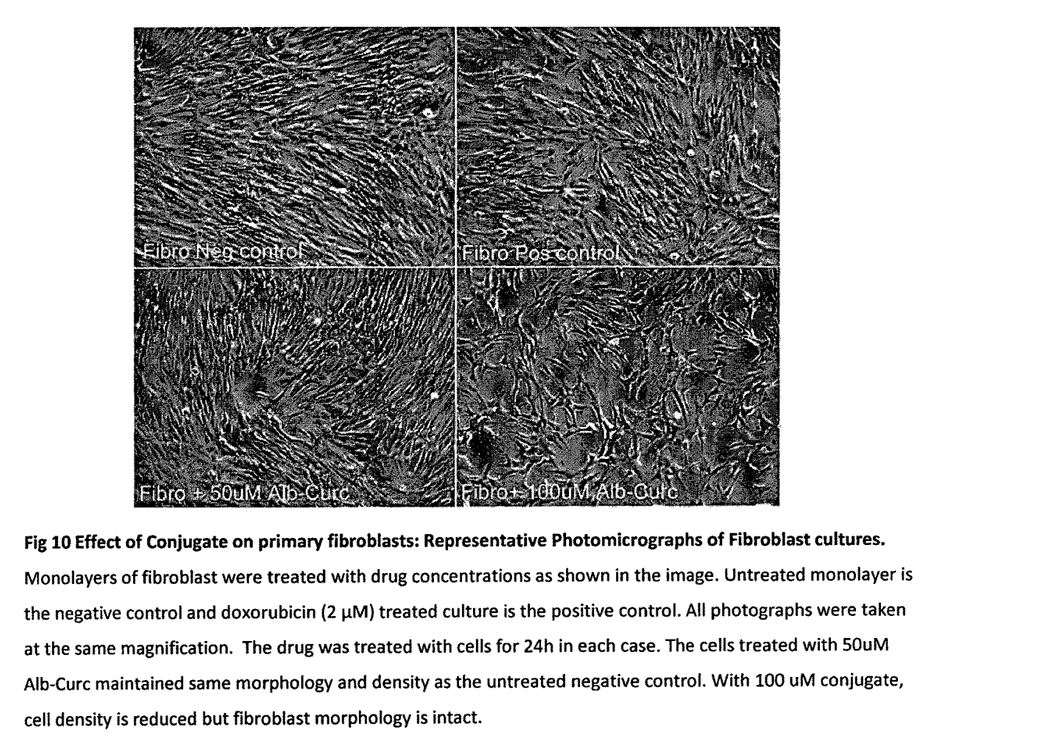
FIG. 10. Effect of conjugate on primary fibroblasts.

The studies were carried out using fibroblasts (FIG. 10) to determine whether the drug (Alb-Cur), or positive control (5-FU) induced any apoptosis. It was observed that the drug did not elicit any toxicity on these cells up to a conc. of 50 µM. But in 100 µM treated cells proliferation was reduced, without any morphological change to the cells.

The UV-Vis, FTIR and Raman spectrum of purified albuminated curcumin conjugate confirmed the strong interaction between curcumin and albumin. No curcumin was detected in the dialysate, thus confirming the stability and non-degradation of the conjugate. The drug showed pronounced apoptosis on lung cancer (A549) and prostate cancer (PC3) cells in a dose and time dependent manner by Annexin V-FITC assay and cell cycle arrest by flow cytometry. The results from cell culture analysis revealed the anti-tumour property of albuminated curcumin. The conjugate also induced cell cycle arrest and apoptotic effect on endothelial cells, which suggested anti-angiogenic property. The optimum non-toxic dose of the drug was identified by treating with human fibroblast cells and analyzing the cell proliferation and apoptosis.

Albumin-curcumin conjugate is stable and highly soluble. Effect of release curcumin is established for their anticancer & antiangiogenic property in in vitro cell culture experiment. Albumin-curcumin conjugate is proposed for systemic infusion and analysis of cancer control.

We claim:

1. A process for the preparation of an albumin-curcumin conjugate, comprising the steps of:
    preparing a solution of 50 mg native Bovine Serum albumin (BSA) in phosphate buffered saline (PBS);
    adding a solution of 2000 µM curcumin in DMSO to the BSA solution at 35 to 39° C. to obtain a reaction mixture comprising the albumin-curcumin conjugate;
    allowing the reaction mixture to stand for 1 to 2 hours, wherein a pH of the reaction is maintained in a range of 6 to 10;
    purifying the albumin-curcumin conjugate by gel filtration of the conjugate in buffer, thereby removing unconjugated curcumin and providing a filtered albumin-curcumin conjugate; and
    lyophilizing the filtered albumin-curcumin conjugate, thereby obtaining a purified, concentrated, and stable albumin-curcumin conjugate.

2. The process as claimed in claim 1, wherein the pH of the reaction is maintained at 7.2.

3. The process as claimed in claim 1, wherein the reaction is effected at a temperature of 37° C.

4. The process as claimed in claim 1, further comprising:
    reconstituting the lyophilized, filtered albumin-curcumin conjugate to obtain a 2000 µM solution.

5. A purified, concentrated, and stable albumin-curcumin conjugate for application in cancer therapy, prepared by the method of claim 1.

6. The albumin-curcumin conjugate as claimed in claim 5, which inhibits growth of cancer cell lines and endothelial cells causing anticancer and anti angiogenic activity, and can be used for the treatment of cancer.

7. The albumin-curcumin conjugate as claimed in claim 5, which acts on lung cancer cell line A549 to induce cell death at a concentration ranging from 50 µM to 100 µM.

8. The albumin-curcumin conjugate as claimed in claim 5, which acts on human prostate cancer cell line PC3 at a concentration ranging from 50 µM to 100 µM.

9. The albumin-curcumin conjugate as claimed in claim 5, which shows anti angiogenic effect at a concentration ranging from 100 µM to 250 µM.

10. The albumin-curcumin conjugate as claimed in claim 5, which acts on human leukemia cell line K562 at a concentration ranging from 500 µM to 1000 µM.

11. A process for the preparation of an albumin-curcumin conjugate consisting of the steps of:
    preparing a solution of 50 mg native Bovine Serum albumin (BSA) in 1 ml phosphate buffered saline (PBS);
    adding 10 µl of a solution of 200 mM curcumin in dimethyl sulfoxide (DMSO) to the BSA solution to obtain a mixture;
    incubating the mixture for 1-2 hours at 37° C. at pH 7.2 to obtain an albumin-curcumin conjugate having a concentration of 2000 µM;
    eluting the conjugate in PBS with a cross-linked dextran gel filtration column, thereby providing a filtered albumin-curcumin conjugate; and
    lyophilizing the filtered albumin-curcumin conjugate.

* * * * *